(12) United States Patent
Zhang

(10) Patent No.: US 8,825,145 B1
(45) Date of Patent: Sep. 2, 2014

(54) BEAT-MORPHOLOGY MATCHING SCHEME FOR CARDIAC SENSING AND EVENT DETECTION

(71) Applicant: Medtronic, Inc., Minneapolis, MN (US)

(72) Inventor: Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/804,816

(22) Filed: Mar. 14, 2013

(51) Int. Cl.
A61B 5/0402 (2006.01)
A61B 5/0452 (2006.01)
A61B 5/0472 (2006.01)

(52) U.S. Cl.
CPC .................. *A61B 5/04525* (2013.01)
USPC ........................... 600/509; 600/515; 600/521

(58) Field of Classification Search
CPC .................................................. A61B 5/04525
USPC ................. 600/509, 515–517, 521
See application file for complete search history.

(56) References Cited

U.S. PATENT DOCUMENTS

| | | | |
|---|---|---|---|
| 4,947,857 A | 8/1990 | Albert et al. | |
| 5,240,009 A | 8/1993 | William | |
| 5,255,186 A | 10/1993 | Steinhaus | |
| 5,259,387 A | 11/1993 | dePinto | |
| 5,779,645 A | 7/1998 | Olson | |
| 7,765,002 B2 | 7/2010 | Ettori | |
| 7,904,153 B2 | 3/2011 | Greenhut | |
| 8,145,307 B2 | 3/2012 | Zhang | |
| 8,160,687 B2 | 4/2012 | Warren | |
| 2002/0193696 A1* | 12/2002 | Hsu et al. | 600/512 |
| 2004/0127945 A1* | 7/2004 | Collins et al. | 607/5 |
| 2004/0230105 A1 | 11/2004 | Geva et al. | |
| 2005/0137485 A1* | 6/2005 | Cao et al. | 600/510 |
| 2010/0185109 A1 | 7/2010 | Zhang | |
| 2011/0270108 A1 | 11/2011 | Stadler et al. | |
| 2012/0046706 A1 | 2/2012 | Anderson | |
| 2012/0130263 A1 | 5/2012 | Pretorius | |
| 2012/0289846 A1 | 11/2012 | Zhang et al. | |

FOREIGN PATENT DOCUMENTS

WO 2006/039694 A2 4/2006

OTHER PUBLICATIONS (PCT/US2014/020500) PCT Notification of Transmittal of the International Search Report and the Written Opinion of the International Searching Authority.

* cited by examiner

*Primary Examiner* — Allen Porter, Jr.
(74) *Attorney, Agent, or Firm* — Michael C. Soldner

(57) ABSTRACT

A medical device and associated method for classifying an unknown cardiac signal operate to sense a cardiac signal over known cardiac cycles and generate a template of the known cardiac cycles. An unknown cardiac signal is sensed over an unknown cardiac cycle. A template alignment point and an unknown cardiac signal alignment point are identified by using a fourth order difference signal. The template and the unknown cardiac signal are aligned across an alignment window by aligning the template alignment point and the unknown cardiac signal alignment point. A morphology match metric measuring a similarity between the aligned template and the unknown cardiac signal is computed.

21 Claims, 8 Drawing Sheets

BEAT-MORPHOLOGY MATCHING SCHEME FOR CARDIAC SENSING AND EVENT DETECTION

CROSS-REFERENCE TO RELATED APPLICATION

Cross-reference is hereby made to the commonly-assigned related U.S. application Ser. Nos. 13/826,097 and 13/826,248, both entitled "A BEAT-MORPHOLOGY MATCHING SCHEME FOR CARDIAC SENSING AND EVENT DETECTION," to Zhang, both filed concurrently herewith and both incorporated herein by reference in it's entirety.

TECHNICAL FIELD

The disclosure relates generally to implantable medical devices and, in particular, to an apparatus and method for performing a matching scheme for comparing cardiac sensed waveforms to a known template.

BACKGROUND

Implantable cardioverter defibrillators (ICDs) often have the capability of providing a variety of anti-tachycardia pacing (ATP) regimens as well as cardioversion/defibrillation shock therapy. Normally, arrhythmia therapies are applied according to a pre-programmed sequence of less aggressive to more aggressive therapies depending on the type of arrhythmia detected. Typically, termination of an arrhythmia is confirmed by a return to either a demand-paced rhythm or a sinus rhythm in which successive spontaneous R-waves are separated by at least a defined interval. When ATP attempts fail to terminate the tachycardia, high-voltage cardioversion shocks may be delivered. Since shocks can be painful to the patient and consume relatively greater battery charge than pacing pulses, it is desirable to avoid the need to deliver shocks by successfully terminating the tachycardia using less aggressive pacing therapies when possible. Whenever necessary, however, life-saving shock therapies need to be delivered promptly in response to tachyarrhythmia detection.

The success of a tachycardia therapy depends in part on the accuracy of the tachycardia detection. In some cases, a tachycardia originating in the atria, i.e. a supraventricular tachycardia (SVT), is difficult to distinguish from a tachycardia originating in the ventricles, i.e. a ventricular tachycardia (VT). For example, both the atrial chambers and the ventricular chambers may exhibit a similar tachycardia cycle length when an SVT is conducted to the ventricles or when a VT is conducted retrograde to the atria. Accordingly, methods are needed for accurately classifying a detected tachycardia as VT or SVT to allow the most appropriate therapy to be delivered by the ICD, with the highest likelihood of success and without unacceptably delaying attempts at terminating the tachycardia.

Tachyarrhythmia detection may begin with detecting a fast ventricular rate, referred to as a rate- or interval-based detection. Before a therapy decision is made, tachyarrhythmia detection may further require discrimination between SVT and VT using cardiac signal waveform morphology analysis, particularly when a fast 1:1 atrial to ventricular rate is being sensed. Among the factors affecting the sensitivity and specificity of a morphology waveform matching scheme are the methods used to align an unknown signal waveform and a known waveform template, the number of sample data points used to compare the unknown and known waveforms, and the matching analysis performed on the aligned, selected sample data points. A need remains for an apparatus and method for providing reliable cardiac beat morphology matching schemes for cardiac event detection.

DETAILED DESCRIPTION

An IMD, or other device, according to the present disclosure determines the morphology of a cardiac cycle signal corresponding to an unknown heart rhythm by determining the amount of morphological similarity between the cardiac cycle signal and a template having a known morphology corresponding to a known heart rhythm. The template may have the morphology of a normal cardiac cycle, e.g., a cardiac cycle of a normal sinus heartbeat for a patient in which the IMD is implanted, or an averaged cardiac cycle based on a plurality of normal cardiac cycles. In some examples, a clinician may generate the template based on data received from the IMD, and then subsequently upload the generated template to the IMD. In other examples, the IMD may automatically generate the template and periodically update the template during operation. Improved techniques are disclosed herein for generating a template, aligning the template with a cardiac cycle signal of an unknown beat, and computing a morphology matching metric of the similarity between the cardiac cycle signal and the template.

Figure 1:
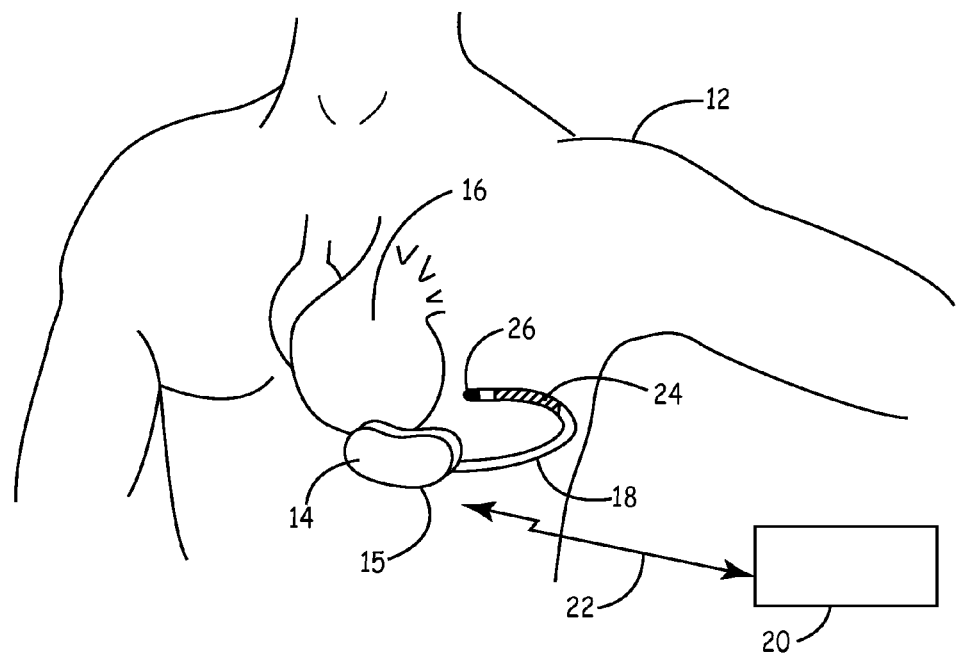
FIG. 1 and FIG. 2 are schematic diagrams of an implantable medical device (IMD) in which methods described herein may be usefully practiced.
Figure 2:
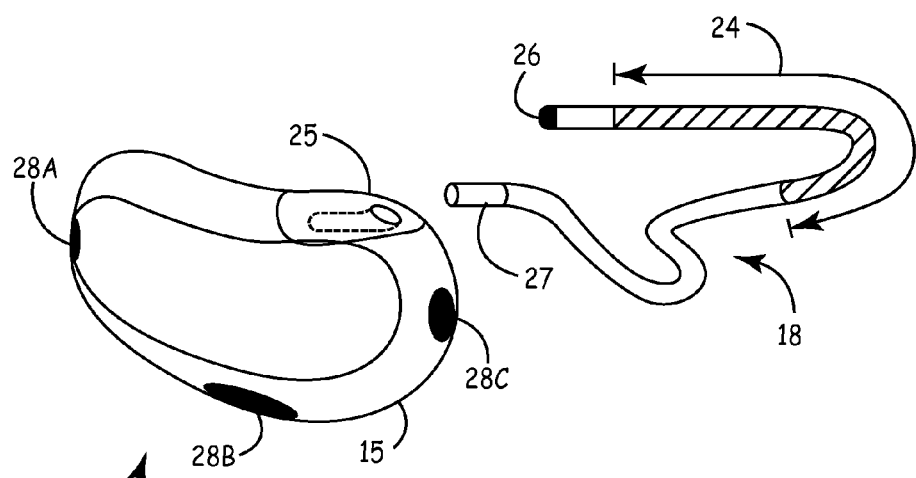

FIG. 1 and FIG. 2 are schematic diagrams of an IMD in which methods described herein may be usefully practiced. As illustrated in FIG. 1, IMD 14 according to one embodiment is subcutaneously implanted outside the ribcage of a patient 12, anterior to the cardiac notch. IMD 14 includes a housing 15 to enclose electronic circuitry of the device 14.

A sensing and cardioversion/defibrillation therapy delivery lead 18 in electrical communication with IMD 14 is tunneled subcutaneously into a location adjacent to a portion of a latissimus dorsi muscle of patient 12. Specifically, lead 18 is tunneled subcutaneously from a median implant pocket of IMD 14 laterally and posteriorly to the patient's back to a location opposite the heart such that the heart 16 is disposed between IMD 14 and a distal electrode coil 24 and a distal sensing electrode 26 of lead 18.

Subcutaneous lead 18 includes a distal defibrillation coil electrode 24, a distal sensing electrode 26, an insulated flexible lead body and a proximal connector pin 27 (shown in FIG. 2) for connection to subcutaneous device 14 via a connector 25. In addition, one or more electrodes 28A, 28B, 28C, collectively 28, (shown in FIG. 2) are positioned along the outer surface of the housing to form a housing-based subcutaneous electrode array (SEA). Distal sensing electrode 26 is sized appropriately to match the sensing impedance of the housing-based subcutaneous electrode array. It is understood that while IMD 14 is shown with electrodes 28 positioned on housing 15, electrodes 28 may be alternatively positioned along one or more separate leads connected to device 14 via connector 25. The lead and electrode configuration shown in FIG. 1 is merely illustrative of one arrangement of electrodes that can be used for sensing subcutaneous ECG signals and delivering cardioversion/defibrillation shocks. Numerous configurations may be contemplated that include one or more housing-based electrodes and/or one or more lead-based electrodes for enabling sensing of an ECG signal using extra-vascular, extra-cardiac electrodes implanted beneath the skin, muscle or other tissue layer within a patient's body.

Further referring to FIG. 1, a programmer 20 is shown in telemetric communication with IMD 14 by an RF communication link 22. Communication link 22 may be any appropriate RF link such as Bluetooth, WiFi, or Medical Implant Communication Service (MICS).

IMD 14 shown in FIGS. 1 and 2 is one illustrative embodiment of the type of device that may be adapted for practicing methods described herein. A subcutaneous IMD system is subject to muscle and other noise and motion artifact due to the subcutaneous placement of electrodes. The methods described herein are well-suited to address accurate cardiac event detection in a subcutaneous IMD system. IMD 14 and associated lead 18 are referred to as a "subcutaneous IMD system" because lead 18 is positioned in an extravascular location, subcutaneously. It is understood that while IMD 14 and lead 28 may be positioned between the skin and muscle layer of the patient, IMD 14 and any associated leads could be positioned in any extravascular location of the patient, such as below the muscle layer or within the thoracic cavity, for example. Furthermore, while illustrative embodiments of the techniques and methods described herein relate to a subcutaneous IMD system, it is contemplated that the disclosed techniques may be useful in other IMD systems configured to detect cardiac arrhythmias utilizing electrodes carried along the IMD housing and/or leads extending therefrom, which may include transvenous and/or extravascular leads carrying any combination of epicardial electrodes, endocardial electrodes or subcutaneous electrodes, for example.

In the illustrative embodiments described herein, the disclosed methods are described in conjunction with an IMD capable of delivering a therapy in response to tachyarrhythmia detection. In alternative embodiments, cardiac event detection methods described herein may be implemented in a monitoring device that does not include therapy delivery capabilities, such as an ECG recording device or an implantable cardiac hemodynamic monitor.

Figure 3:
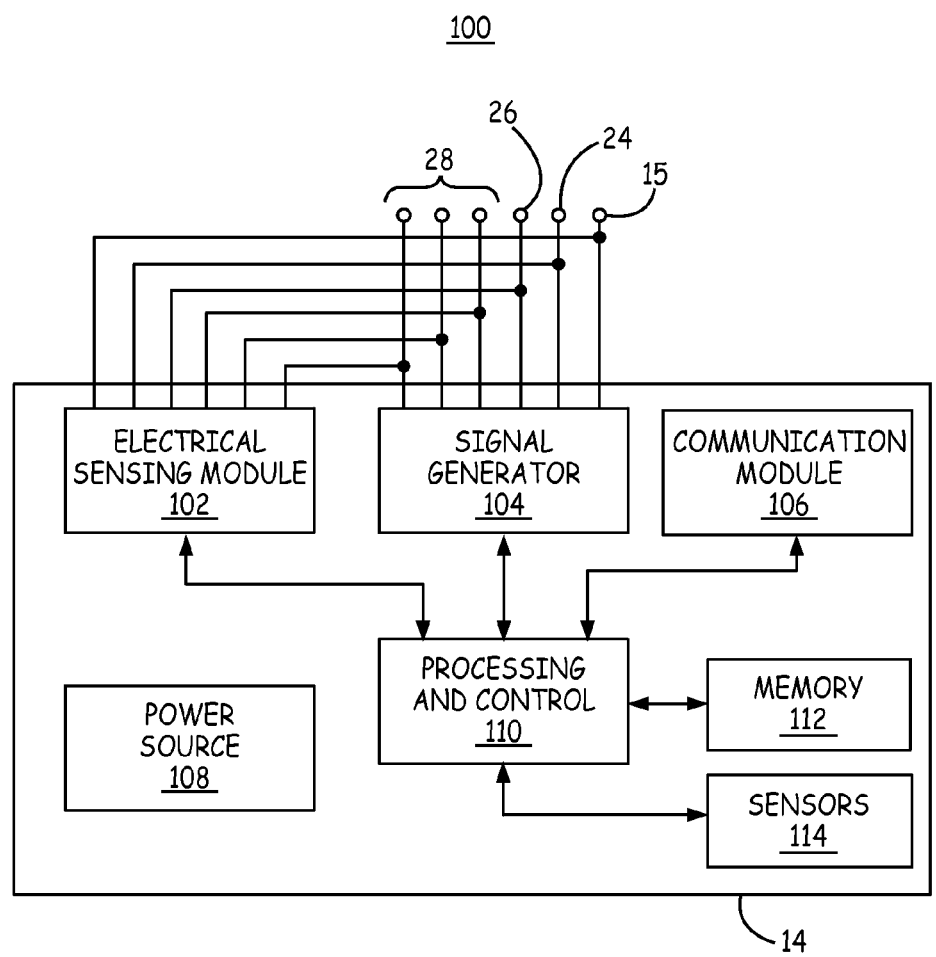
FIG. 3 is a functional block diagram of electronic circuitry that is included in one embodiment of IMD 14 shown in FIG. 1 for practicing the methods described herein.

FIG. 3 is a functional block diagram 100 of electronic circuitry that is included in one embodiment of IMD 14 shown in FIG. 1 for practicing the methods described herein. The IMD 14 includes electrical sensing module 102, signal generator module 104, communication module 106, processing and control module 110 and associated memory 112, and a power source 108 for powering each of the modules 102, 104, 106, 110 and memory 112. Power source 108 may include one or more energy storage devices, such as one or more primary or rechargeable batteries. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Modules included in IMD 14 represent functionality that may be included in IMD 14 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Furthermore, memory 112 may include non-transitory computer readable media storing instructions that, when executed by one or more processing circuits, cause the modules to perform various functions attributed to the modules herein. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components.

Processing and control module 110 communicates with signal generator module 104 and electrical sensing module 102 for sensing cardiac electrical activity and generating cardiac therapies in response to sensed signals. Signal generator module 104 and electrical sensing module 102 are electrically coupled to subcutaneous SEA electrodes 28 incorporated along but electrically insulated from IMD housing 15, lead-based electrodes 24 and 26 and housing 15, at least a portion of which also serves as a common or ground electrode and is therefore also referred to herein as "housing electrode" 15.

Electrical sensing module 102 is configured to monitor signals from available electrodes 26 and 28 in order to monitor electrical activity of a patient's heart. Electrical sensing module 102 may selectively monitor any sensing vector selected from electrodes 26 and 28. Sensing module 102 may include switching circuitry for selecting which of electrodes 24, 26, 28 and housing electrode 15 are coupled to sense amplifiers included in sensing module 102. Switching circuitry may include a switch array, switch matrix, multiplexer, or any other type of switching device suitable to selectively couple sense amplifiers to selected electrodes. Sensing vectors will typically be selected from SEA electrodes 28 in combination with lead-based sensing electrode 26 although it is recognized that in some embodiments sensing vectors may be selected that utilize coil electrode 24 and/or housing electrode 15.

Processing and control 110 processes the subcutaneous ECG sense signals received from sensing vectors selected from SEA 28 (FIG. 2) and sensing electrode 26. Some aspects of sensing and processing subcutaneous ECG signals are generally disclosed in commonly-assigned U.S. Pat. No. 7,904,153 (Greenhut, et al.), hereby incorporated herein by reference in its entirety.

Electrical sensing module 102 may include signal conditioning circuits, e.g., amplification and filtering circuits that amplify and filter cardiac electrical signals received from electrodes 26 and 28. Electrical sensing module 102 includes analog-to-digital (ND) conversion circuits that digitize the conditioned cardiac electrical signals. The digitized data generated by the ND circuits included in electrical sensing module 102 may be referred to as "raw data." In some examples, the A/D circuits may include an 8-bit ND converter that samples conditioned cardiac electrical signals at approximately 256 Hz. Sensing module 102 generates R-wave sense signals upon sensing an R-wave from the ECG signal, for example based on an auto-adjusted threshold crossing of the ECG signal. The timing of an R-wave sense signal is used by processing and control module 110 to measure R-R intervals and for selecting sample points buffered in memory for use in morphology matching algorithms.

In some embodiments, sensing module 102 may include multiple sensing channels having different sensing bandwidths. The different sensing channels may be coupled to the same or different sensing electrode vectors selected from SEA electrodes 28 and lead-based sensing electrode 26. In one embodiment, sensing module 102 includes a wide-band channel having a bandwidth of approximately 2.5 Hz to 95 Hz and a narrow-band channel having a sensing bandwidth between 2.5 Hz and 23 Hz. The wide band channel may be used for sensing R-waves and generating R-wave sense signals. The narrow band channel may be used for providing digitized raw ECG signals to processing module 110 for performing morphology analysis. Alternatively, the wide band channel or the narrow band channel may be used alone or in combination for performing the morphology analysis.

Processing module 110 receives raw data from electrical sensing module 102 and detects cardiac tachyarrhythmias based on the raw data and processing thereof. Detection of a malignant tachyarrhythmia is determined by processing and control module 110 based on sensed cardiac event signals determined from one or more selected ECG signals. R-wave sense event signals and a digitized ECG signal may be output from sensing module 102 to processing and control module 110. Processing and control module 110 performs tachyarrhythmia detection algorithms using the R-wave sense event signals and digitized ECG signal to detect a treatable heart rhythm. As further described below, a detection algorithm may use a combination of intervals measured between successively sensed R-waves (i.e. R-R intervals) and ECG waveform morphology analysis for detecting and discriminating heart rhythms. For example, processing and control module 102 may detect tachyarrhythmias using a rate-based detection algorithm in which processing and control module 102 monitors R-R intervals and identifies a tachyarrhythmia when a predetermined ratio of R-R intervals are shorter than a threshold interval.

When a fast heart rate is detected by the processing and control module 110 based on sensed R-R intervals, processing and control module 110 may be programmed to perform a morphology analysis to discriminate between supraventricular tachycardia (SVT) and VT or VF. The morphology analysis is generally based on comparison of data obtained from an ECG signal of an unknown cardiac beat to a known cardiac beat template, e.g. a known normal sinus rhythm template. Accordingly, processing and control module 110 is configured to generate a morphology template of a known beat and store the template in memory 112.

As further described herein, processing and control module 110 operates to determine a fourth order difference signal from the raw sensed ECG signal received from sensing module 102. This fourth order difference signal is determined as the difference between the amplitude of a given ECG signal sample point and the sample point occurring four sampling intervals earlier. The fourth order difference signal sample points derived from the ECG raw signal may be expressed as $x(n+4)-x(n)$.

This fourth order difference signal is used to align an ECG signal from an unknown beat to a known template. The fourth order difference signal is further compared to the stored template to determine a similarity between the fourth order difference signal and the known template in some embodiments. The similarity is measured by a morphology matching metric which may be computed using a variety of techniques. In one embodiment, a normalized waveform area difference (NWAD) is computed from the fourth order difference signals of an unknown beat and the template. The unknown beat is classified as being either a supraventricular beat or a beat that is ventricular in origin in response to the morphology matching metric.

It should be noted that implemented tachyarrhythmia detection algorithms may utilize not only ECG signal analysis methods but may also utilize supplemental sensors 114, such as tissue color, tissue oxygenation, respiration, patient activity, heart sounds, and the like, for contributing to a decision by processing and control module 110 to apply or withhold a defibrillation therapy.

In response to detecting a treatable cardiac rhythm, processing and control module 110 controls signal generator module 104 to generate and deliver a cardioversion or defibrillation shock pulse to the patient's heart via electrodes 24 and 15. Generally, a treatable rhythm is identified as ventricular tachycardia (VT) or ventricular fibrillation (VF), which may be successfully terminated by a shock therapy. A tachycardia originating in the atria, i.e. a supraventricular tachycardia (SVT), is generally not treated by delivery of a shock therapy by the IMD 14. As further described herein, a treatable rhythm is identified by using morphology analysis to discriminate between fast heart rhythms originating in the atria and fast heart rhythms originating in the ventricles. This discrimination is performed by determining the similarity between an unknown cardiac signal and a known template. For example, an unknown cardiac signal or "beat" may be classified as an SVT beat if the morphology matching metric exceeds a matching threshold when compared to a normal sinus rhythm template. The unknown cardiac signal is classified as a VT/VF beat if the morphology matching metric falls below a matching threshold.

Processing and control module 110 may control signal generator module 104 to deliver a shock therapy using coil electrode 24 and housing electrode 15 according to one or more therapy programs, which may be stored in memory 112. For example, processing and control module 110 may control signal generator module 104 to deliver a shock pulse at a first energy level and increase the energy level upon redetection of a VT or VF rhythm. Shock pulse generation and control is further described in the above incorporated '153 Greenhut patent.

Communication module 106 includes any suitable hardware, firmware, software or any combination thereof for communicating with another device, such as an external programmer 20 and/or a patient monitor. Under the control of processing module 110, communication module 106 may receive downlink telemetry from and send uplink telemetry to programmer 20 and/or a patient monitor with the aid of an antenna (not shown) in IMD 14.

Processing and control module 102 may generate marker channel data based on analysis of the raw data. The marker channel data may include data that indicates the occurrence and timing of sensing, diagnosis, and therapy events associated with IMD 14. Processing and control module 110 may store the generated marker channel data in memory 112. Although not illustrated, in some examples, marker channel data may include information regarding the performance or integrity of IMD 14, including power source 108 and lead 18.

Processing and control module 110 may store raw data and marker channel data in memory 112. For example, processing and control module 110 may continuously store raw data from one or more electrode combinations in memory 112 as the raw data is received from electrical sensing module 102. In this manner, processing and control module 110 may use memory 112 as a buffer to store a predetermined amount of raw data. In some examples, processing and control module 110 may store raw data corresponding to a predetermined number of cardiac cycles, e.g., 12 cycles. In other examples, processing and control module 110 may store a predetermined number of samples of raw data, e.g., processing module 110 may store raw data for a predetermined period of time.

Processing and control module 110 may perform analysis on the raw data stored in memory 112. For example, analysis may include deriving a fourth order difference signal from the raw ECG signal for an unknown cardiac cycle, determining an alignment point of the fourth order difference signal for alignment with a previously established template of a known beat type, aligning the unknown cardiac cycle signal using the alignment point with the template by shifting sample points to align the alignment point derived from the fourth order difference signal with a template alignment point, and computing a morphology match metric, e.g. a NWAD, of the aligned signal and template. The value of the morphology match metric is used to classify the beat as an SVT or a ventricular beat corresponding to a ventricular tachyarrhthmia (VT or VF). A threshold number of VT/VF beats may be required for processor and control module 110 to control signal generator 104 to generate and deliver a shock pulse.

Processing and control module 110 may store a selected number of sample points before and after each R-wave sense signal received from sensing module 102 in a buffer in memory 112. For example, processing and control module 110 may store approximately 26 data points before the R-wave sense signal and 26 data points after the R-wave sense signal for each cardiac cycle. The 26 data points before and after the R-wave sense signal defines an alignment window. The fourth order difference signal is determined from these buffered sample points across the alignment window and these points are aligned with the template based on an alignment point identified within the alignment window of the fourth order difference signal.

The morphology matching metric is computed by processing and control module 110 using a subset of the fourth order difference signal sample points within the alignment window. The processing and control module 110 measures an R-wave width from the fourth order difference signal and determines a number of sample points to use for computing the morphology match metric based on the fourth order difference signal R-wave width for the current beat. These techniques are further described in conjunction with the flow charts presented herein with continued reference to functional block diagram 100.

Figure 4:
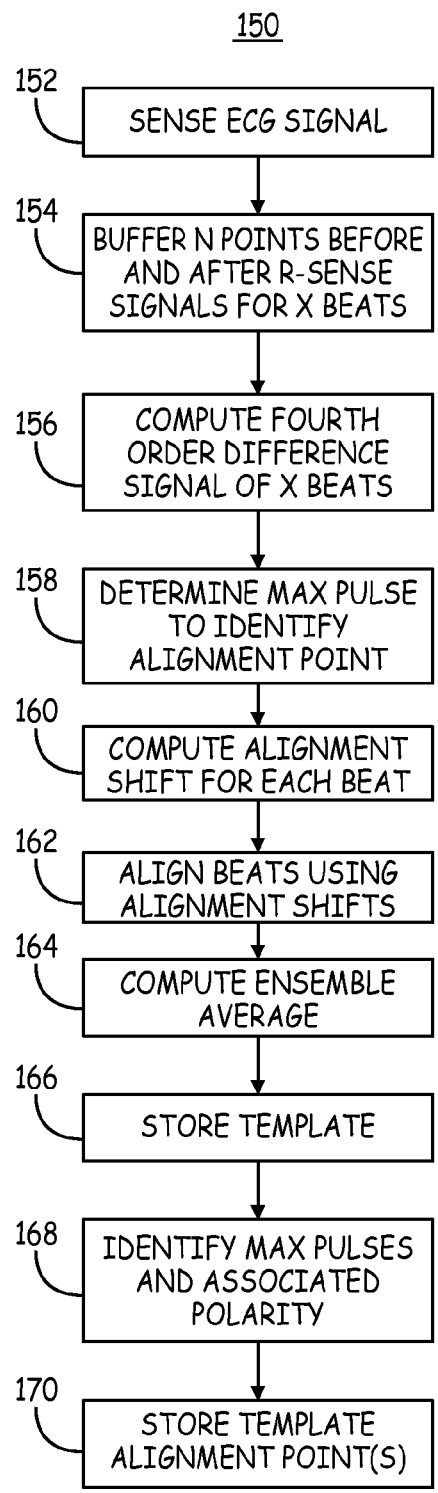
FIG. 4 is a flow chart of a method for establishing a morphology template according to one embodiment.

FIG. 4 is a flow chart 150 of a method for establishing a morphology template according to one embodiment. At block 152, the subcutaneous ECG signal is sensed by sensing module 102 using one or more electrode vectors selected from electrodes 26 and 28. Different morphology templates may be established for different sensing vectors and used for comparison to unknown beats sensed from a respective sensing vector. For example, a template may be established for a sensing vector between electrodes 28a and 26, a sensing vector between electrodes 28b and 26, and a sensing vector between electrodes 28c and 26, referred to respectfully as ECG1, ECG2 and ECG3. During cardiac monitoring, if the ECG1 sensing vector is used to sense cardiac signals, the template established for ECG1 will be used to perform morphology matching analysis and so on.

One or more sensing vectors may be available depending on the particular lead and electrode configuration being used. For example, one or more housing-based electrodes may be available and/or one or more extravascular lead-based electrodes may be available for selecting various combinations of subcutaneous ECG sensing vectors using any combination of one or more housing-based electrodes and/or lead-based electrodes.

A sensing vector may be coupled to one or more sensing channels in sensing module 102. For example, sensing module 102 may include multiple sensing channels having different frequency bandwidths. A selected sensing vector may be coupled to a narrow-band channel and/or a wide-band channel when multiple frequency bandwidth channels are available. Techniques described herein may use a template generated from a relatively wide-band sensing channel or a relatively narrow-band sensing channel for determining similarity between an unknown beat and a known template.

At block 154, a desired number of sample points from the raw ECG signal are buffered in memory 112. The buffered sample points include n points, for example 26 points, prior to and after an R-wave sense signal, for a total of 53 sample points centered on the R-wave sense signal. These sample points centered on the R-wave sense signal define an alignment window which is used in aligning a desired number of cardiac cycles for generating the template.

Sample points are stored for a desired number of cardiac cycles to be used in generating a morphology template, for example 10 cardiac cycles (corresponding to ten sensed R-waves). The sample points acquired at block 154 are stored from cardiac cycles identified during a known cardiac rhythm. For example, the sample points may be stored during a normal sinus rhythm (NSR) that is verified based on regular R-R intervals typical of NSR. In other embodiments, morphology templates may be established at multiple heart rates and/or different known rhythms.

The cardiac cycles selected for buffering in memory 112 may be selected automatically by processing and control module 110 based on R-R intervals, noise analysis, or other criteria. In other embodiments, the desired number of cardiac cycles is identified manually by a clinician through visual analysis of ECG signals transmitted by communication module 106 to programmer 20. Accordingly, some aspects of the techniques described herein may be performed by a processor included in programmer 20 using data retrieved from IMD 14. The programmer 20 may perform the computations necessary to establish a morphology template for one or more ECG sensing vectors and the template data may be transmitted to communication module 106 by wireless telemetry and stored in memory 112.

At block 156, the fourth order difference signal for each of the stored cardiac cycles is computed from the buffered sample points. The fourth order difference signal is used in processing subcutaneous ECG signals to enhance the ECG signal frequency components in the range between approximately 13 and 41 Hz, which is the frequency range containing the most energy of the subcutaneous ECG signal.

In contrast, intracardiac electrogram (EGM) signals sensed using intracardiac electrodes carried by transvenous leads, for example, will contain a higher energy component at a higher frequency bandwidth, making morphology waveform analysis of EGM signals more sensitive to high frequency noise, such as muscle noise and electromagnetic interference. A second order difference equation has been proposed to be applied to EGM signals to reduce the high frequency noise effects. Reference is made to commonly-assigned pre-grant U.S. Publication No. 2012/0289846 (Zhang et al.). Additionally, when a wavelet morphology analysis is performed on the EGM signal, the waveform is decomposed into different frequency components, for example 5 frequency components. The contribution of the lower frequency components becomes amplified in the decomposed waveform. The proposed second order difference equation attenuates the artificially exaggerated low frequency components and attenuates the high frequency (noise) components in the wavelet analysis of the EGM signal.

The fourth order difference signal of the raw subcutaneous ECG signal, on the other hand, provides attenuation of very low frequency components, near baseline such as baseline wander, to enhance the relatively low frequency signal content in the ECG signal. The morphology analysis of the ECG signal is less sensitive to high frequency noise than the intracardiac EGM signal because of the higher energy content in a relatively lower frequency bandwidth than the higher frequency bandwidth of the EGM signal. Accordingly, the fourth order difference signal is derived from the raw ECG signal to address the unique challenges of aligning the ECG sample points and to enhance the low frequency signal content while attenuating very low frequency content to improve morphology analysis outcomes.

At block 158, the maximum pulse of the fourth order difference signal for each beat is identified. To identify pulses within the alignment window, pulse criteria may be established, such as a pulse width equal to at least some minimum number of sample points and a pulse amplitude of at least some minimum amplitude. The pulse having the maximum absolute amplitude is identified as being the dominant pulse of the fourth order difference signal, and its polarity (positive or negative) is determined. As used herein, the "dominant pulse" refers to the pulse having a maximum absolute peak amplitude within the alignment window. The maximum peak of the dominant pulse within the alignment window is defined as the alignment point for the given cycle. It is contemplated that other features of the fourth order difference signal could be identified to use as alignment points. For example, a zero crossing of the dominant pulse in the fourth order difference signal could be an alternative alignment point.

The dominant pulse maximum peak amplitude sample points having the same polarity are identified from each of the X cycles of sample points as alignment points. The X cycles are aligned by choosing one cycle as a reference then determining an alignment shift for each of the other X−1 cycles. The alignment shift is computed for a given cycle as the sample point difference between the alignment point of the reference cycle and the alignment point of the given cycle. The raw digitized data signal for each cycle is shifted over the alignment window by the alignment shift for the respective cycle. Alternatively, the fourth order difference signals are aligned over the alignment window based on the identified alignment points.

Once aligned, the X cycles of signal sample points are ensemble averaged to obtain a template at block 164 for the known cardiac beat type. In one embodiment, the template is an ensemble average of the raw ECG signal sample points for each beat after aligning the raw ECG signal samples for each beat using the computed alignment shift for each beat, derived from the fourth order difference signals. In other words, the alignment shifts are computed as a number of sample points required to align a fourth order difference signal maximum pulse with a fourth order difference maximum pulse of the reference cycle, where both maximum pulses have the same polarity, and this shift is applied to the ECG signal. Alternatively, the alignment shifts are applied to the fourth order difference signals and the template is computed as an ensemble average of the aligned fourth order difference signals. In some embodiments, templates of both the raw ECG signal and the fourth order difference signal are generated.

The fourth order difference signal is therefore used to align the sample points of either the raw ECG signal for X beats or the fourth order difference signal for X beats. Those aligned X beats are then ensemble averaged to establish a known morphology template. The template is stored at block 166. Templates may be generated and stored for one or more selected ECG sensing vectors as mentioned previously.

At block 168, a template alignment point is identified which will be used to align the template with the unknown cardiac cycle signals during morphology analysis performed for tachyarrhythmia detection. In one embodiment, the fourth order difference signal of the template is computed, when the template is the ensemble average of the raw ECG signal. A template alignment point, such as the maximum pulse peak amplitude point, and its respective polarity are identified. This template alignment point (and polarity) is stored at block 170 in memory 112.

Figure 5:
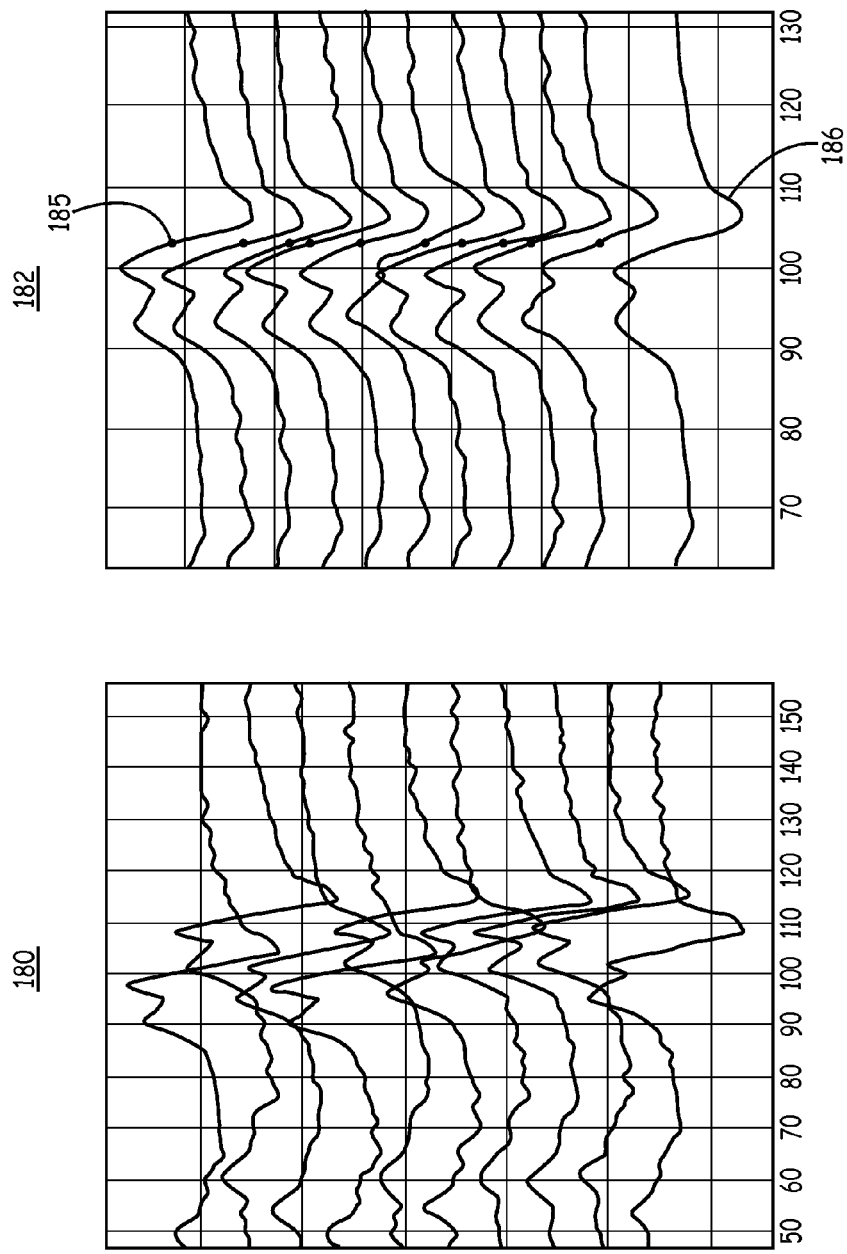
FIG. 5 is example recordings of ECG signal waveforms aligned using two different techniques.

FIG. 5 is example recordings 180 and 182 of ECG signal waveforms aligned using two different techniques. The same subcutaneous ECG recordings 180 and 182 for 10 cardiac cycles are shown in the right and left panels, the right panel having a different vertical scale than the left panel. As can be seen in recordings 180, the R-wave has a double peak in this example in all ten cycles. The double peak is more pronounced in some cycles than in others, and the first peak is sometimes greater than and sometimes less than the second peak. The recordings 180 shown in the left panel are aligned in time based on the timing of the R-wave sense signal for each beat. As can be observed, considerable "jittering" of the R-wave is present when the signals are aligned based on the R-wave sense signal. Similarly, waveform alignment based on a peak amplitude of the raw ECG signal will result in considerable variation in the alignment point within the R-wave.

To address this variation in alignment of R-waves, the fourth order difference signal is generated for each cycle and a maximum pulse peak amplitude sample point is identified as an alignment point rather than the R-wave sense signal point. The maximum pulse peak amplitude sample points having the same polarity are selected for aligning the ten cycles. As described above, an alignment shift is computed for each of the cycles relative to a reference cycle. The raw ECG signal may then be aligned by aligning the maximum pulse peak amplitudes of the fourth order difference signals as shown in the recordings 182 in the right panel.

In the right panel, the same ten raw ECG signals are shown (smaller vertical scale) with the alignment points 185 identified from the fourth order difference signal (not shown) all aligned. Using an alignment point from the fourth order difference signal alleviates alignment error that can result from using an R-wave sense signal or other alignment points identified from the raw ECG signal. The template 186 is computed as the ensemble average of the ECG signal recordings 182 aligned based on the maximum pulse peak amplitude of the fourth order difference signals for each of the ten cycles.

Figure 6:
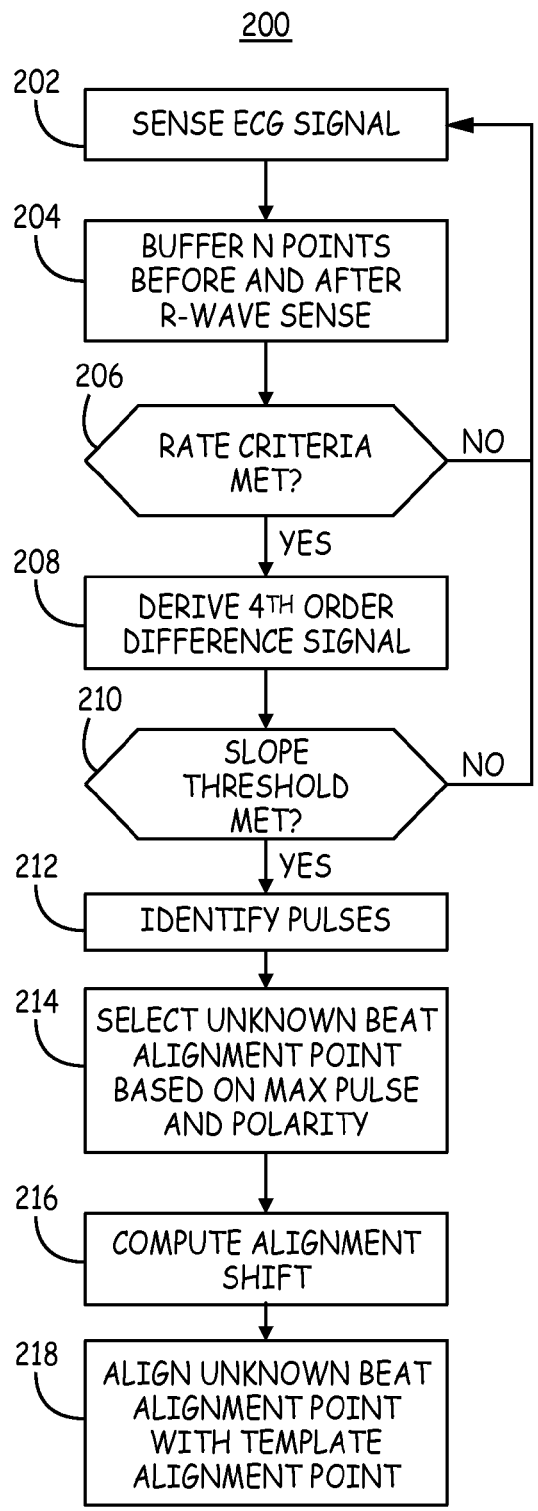
FIG. 6 is a flow chart of a method for aligning an ECG signal of an unknown beat with a known morphology template.

FIG. 6 is a flow chart 200 of a method for aligning an ECG signal of an unknown beat with a known morphology template. At block 202, the ECG signal is sensed by sensing module 102 using an electrode vector, for example selected from electrodes 28 and 26. As described above, the processing and control module 110 receives digitized ECG signals and R-wave sense signals from the sensing module 102 and stores n points before and n points after the sample point on which the R-wave sense occurs in a buffer in memory 112. The 2n+1 sample points define an alignment window within which an alignment point will be identified for alignment with the established template. In one embodiment, the alignment window is 53 sample points centered on the R-wave sense point. These sample points are stored in a memory buffer at block 204.

In some embodiments, the buffered signals will be used to perform morphology analysis when a fast heart rate is detected. Accordingly, at decision block 206, the processing and control module 110 may determine if a fast rate is being detected based on tachyarrhythmia detection criteria, for example a minimum ratio of R-R intervals shorter than a tachyarrhythmia detection interval. If a fast rate is not being detected, the ECG signal sensing continues without performing beat alignment for morphology analysis.

The application of rate criteria at block 206 prior to performing a morphology analysis, however, is optional in that the techniques described herein for establishing a known template, aligning an unknown beat with the established template and computing a morphology metric as a measure of the similarity between the template and the unknown beat may be integrated into a tachyarrhythmia detection algorithm in a variety of ways. The morphology analysis may therefore be initiated or triggered in response to a variety of sensed events or conditions; a fast rate based trigger being just one example of how the morphology analysis techniques may be incorporated in a tachyarrhythmia detection algorithm.

If the rate criteria or other morphology analysis triggering condition is detected, the processing and control module 110 computes a fourth order difference signal at block 208 from the buffered signal sample data. The maximum slope of the fourth order difference signal may be determined at block 210 and compared to a threshold, e.g. approximately 136 analog-to-digital (A/D) conversion units. If the slope threshold is not met, the signal may be rejected as a weak signal and no further analysis of that beat is performed. If the maximum slope is greater than the threshold, at least one pulse corresponding to an R-wave is likely to be present in the alignment window If a slope threshold is met at block 210, pulses within the alignment window are identified at block 212. The number of pulses identified, or lack thereof, within the alignment window may be used to reject a "cardiac cycle" as a noisy cycle or a weak signal. One or more pulses, including negative-going and positive-going pulses, may be identified according to amplitude and pulse width criteria. In some examples, a pulse may be identified based on a slope, maximum peak amplitude (positive or negative), pulse width or any combination thereof. If a threshold number of pulses is identified within the alignment window, the cycle may be considered a noisy cycle. While not shown explicitly in FIG. 6, a noisy cycle may be flagged or rejected for use in morphology analysis.

After identifying all pulses from the fourth order difference signal in the alignment window, a pulse having a maximum pulse amplitude and having the same polarity as the template alignment point is identified at block 214. The sample point having the maximum pulse amplitude (absolute value) that also matches the polarity of the template alignment point is identified and defined as the unknown signal alignment point.

An alignment shift is computed at block 216 as the difference in sample point number between the alignment point identified at block 214 and the previously established template alignment point. The alignment shift is the number of sample points, that the unknown beat must be shifted in order to align the unknown signal alignment point with the template alignment point. The alignment shift is applied at block 218 by shifting the unknown beat sample points to align the unknown beat and the template over the alignment window. The alignment shift may be applied to the fourth order difference signal itself if the template is stored as an ensemble average of aligned fourth order difference signals or stored as the fourth order difference signal of an ensemble average of aligned raw ECG signals. The alignment shift may additionally or alternatively be applied to the digitized raw signal sample points of the unknown signal when the template is the ensemble average of the raw signal sample points acquired during a known rhythm and aligned using the fourth order difference signal as described above in conjunction with FIGS. 4 and 5. In another variation, the template may be the fourth order difference signal of the ensemble averaged raw signals, and the fourth order difference signal of the unknown raw signal is aligned with the fourth order difference template.

Fourth order difference signals computed for deriving a template alignment point and the unknown cardiac signal alignment point may be computed using signals sensed from either a narrow-band channel or a wide-band channel when different frequency bandwidth channels are included in sensing module 102. The alignment points may then be applied to a template derived from either the narrow-band or the wide-band channel and the unknown cardiac signal sensed from the corresponding narrow-band or wide-band channel. As such, different frequency bandwidth channels may be used in various combinations for generating a template, identifying alignment points and measuring a similarity between an unknown cardiac cycle signal and the template.

Figure 7:
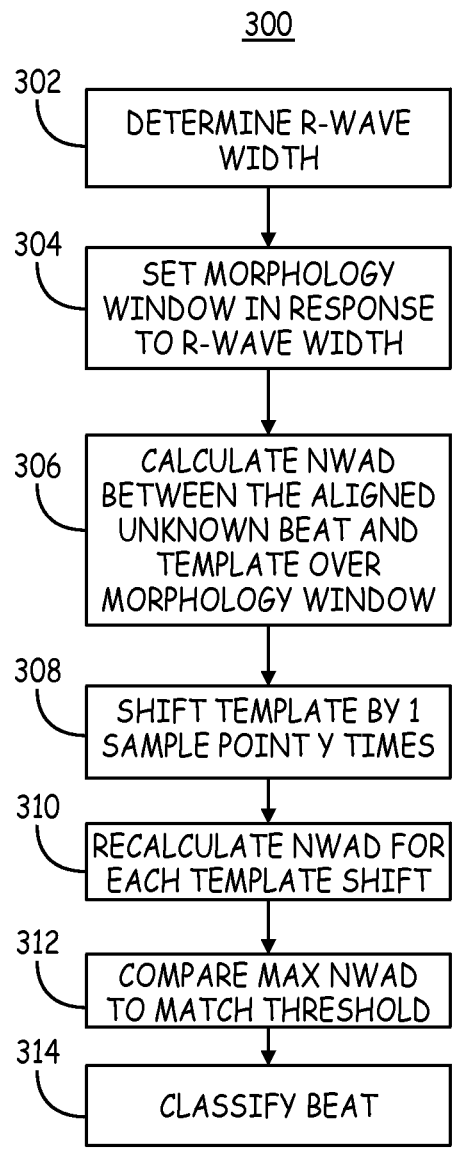
FIG. 7 is a flow chart of a method for computing a morphology metric to determine the similarity between a known template aligned with an unknown cardiac cycle signal according to one embodiment.

FIG. 7 is a flow chart 300 of a method for computing a morphology metric to determine the similarity between a known template aligned with an unknown cardiac cycle signal according to one embodiment. After aligning the unknown cardiac cycle signal, also referred to herein as the "unknown beat" and the template using the fourth order difference signal alignment points, the morphology between the unknown beat and the template is compared. Numerous types of morphology analysis could be used, such as wavelet analysis, comparisons of fiducial points (peak amplitude, zero crossings, maximum slopes, etc.) or other techniques. In one embodiment, a NWAD is computed using a morphology analysis window that is a subset of, i.e. a number of sample points less than, the alignment window.

The operations performed by the processing and control module 110 as described in conjunction with FIG. 7 may be performed on the aligned raw signal and corresponding template and/or the aligned fourth order difference signal and corresponding fourth order difference signal template. At block 302, the R-wave width of the unknown signal is determined. The R-wave width may be measured using a number of techniques.

In an illustrative embodiment the maximum positive pulse and the maximum negative of the fourth order difference signal are identified. The maximum positive pulse is an identified pulse having positive polarity and maximum positive peak value; the maximum negative pulse is an identified pulse having negative polarity and maximum absolute peak value. If the R wave has a positive polarity in the raw ECG signal, the maximum positive pulse will precede the maximum negative pulse on the $4^{th}$-order difference waveform. An onset threshold is set based on the amplitude of the maximum positive pulse and an offset threshold is set based on the amplitude of the maximum negative pulse. For example, one-eighth of the peak amplitude of the maximum positive pulse may be defined as the onset threshold and one eighth of the negative peak amplitude of the maximum negative pulse may be defined as the offset threshold.

The onset of the R-wave is identified as the first sample point to the left of the maximum positive pulse (e.g. moving from the pulse peak backward in time to preceding sample points) to cross the onset threshold. The offset of the R-wave is identified as the first sample point to the right of the maximum negative pulse crossing the offset threshold. The R-wave width is the difference between the onset sample point number and the offset sample point number, i.e. the number of sampling intervals between onset and offset.

Figure 9:
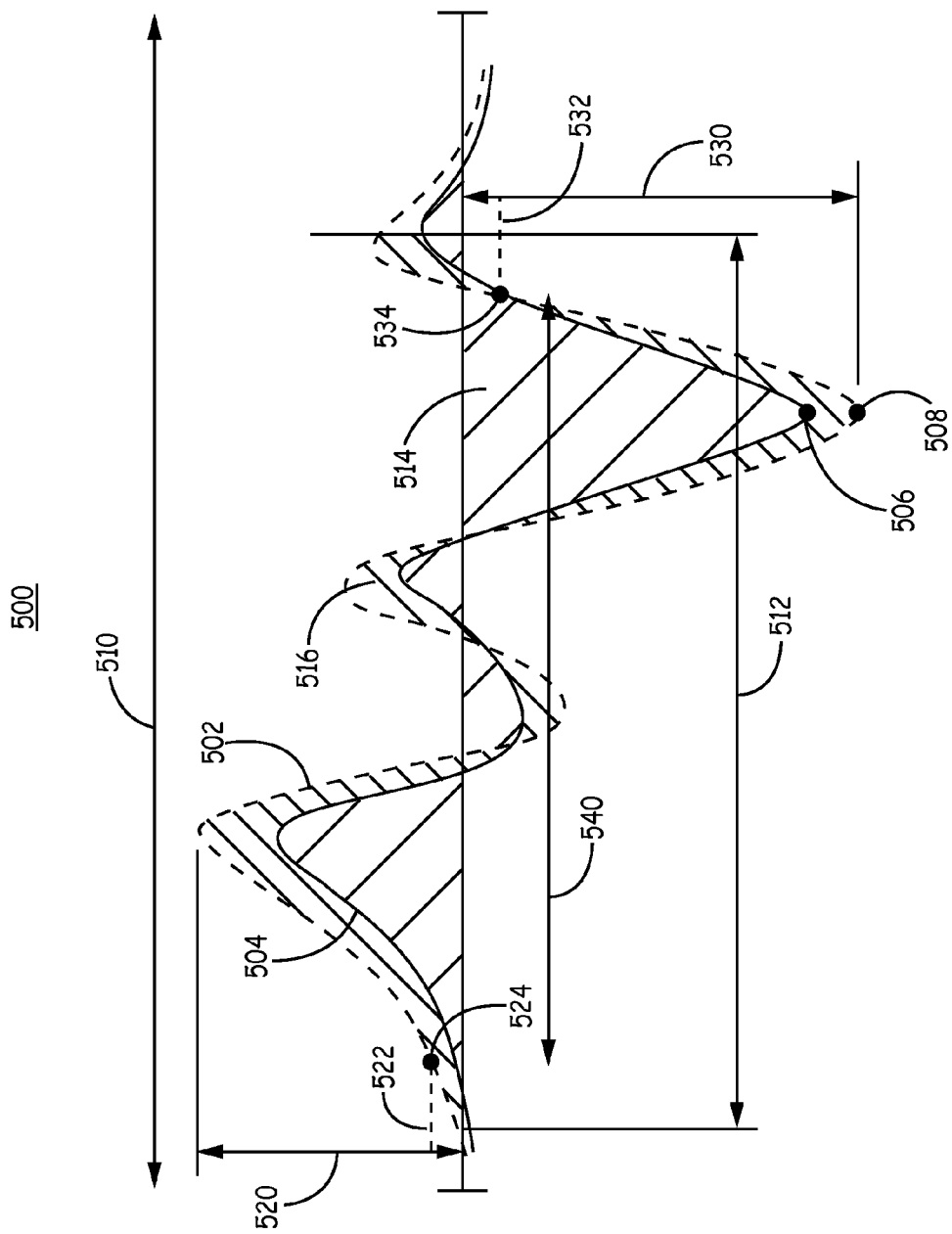
FIG. 9 is a plot of an unknown fourth order difference signal aligned with a fourth order difference template illustrating a technique for determining an R-wave width and computing a NWAD according to another embodiment.

For an R-wave having a negative polarity on the raw waveform, the maximum negative pulse will precede the maximum positive pulse on the fourth order difference signal. As such, the onset threshold is set as a proportion of the maximum negative peak amplitude of the maximum negative pulse of the fourth order difference signal, and the offset threshold is set as a proportion of the maximum positive peak amplitude of the maximum positive pulse. The R-wave onset is detected as the first sample point to cross the onset threshold when moving left (earlier in time) from the maximum negative peak. The R-wave offset is detected as the first sample point to cross the offset threshold moving right (later in time) from the maximum positive peak. The R-wave width is the difference between the onset sample point and the offset sample point. This method of computing an R-wave width based on onset and offset points identified from the fourth order difference signal is illustrated in FIG. 9

The morphology analysis window is set at block 304 in response to the R-wave width determined from the fourth order difference signal. The morphology of the R-wave itself is of greatest interest in classifying the unknown beat. Processing time can be reduced by comparing only the sample points of greatest interest without comparing extra points, for example baseline points or Q- or S-wave points, preceding or following the R-wave. The morphology analysis window is therefore a proportion of the sample points that is less than the total number of sample points aligned in the alignment window.

In one embodiment, different ranges of R-wave width measurements may be defined for which different respective sample numbers will be used to set the morphology analysis window. For example, if the R-wave width is greater than 30 sample intervals, the morphology analysis window is set to a first number of sample points. If the R-wave width is greater than 20 sample intervals but less than or equal to 30 sample intervals, the morphology analysis window is set to a second number of sample points less than the first number of sample points. If the R-wave width is less than or equal to 20 sample points, the morphology analysis window is set to a third number of sample points less than the second number of sample points. Two or more R-wave width ranges may be defined, each with a corresponding number of sample points defining the morphology analysis window. At least one of the R-wave width ranges is assigned a number of sample points defining the morphology analysis window to be less than the alignment window. In some embodiments all of the R-wave width ranges are assigned a number of sample points defining the morphology analysis window to be less than the alignment window.

In the example given above, the alignment window is 53 sample points. If the R-wave width is greater than 30 sample intervals, the morphology window is defined to be 48 sample points. The morphology analysis window may include 23 points preceding the R-wave sense point, the R-wave sense point itself, and 24 points after the R-wave sense point. If the R-wave width is greater than 20 but less than or equal to 30 sample intervals, the morphology window is defined to be 40 sample points (e.g. 19 before the R-wave sense point and 20 after the R-wave sense signal). If the R-wave width is less than or equal to 20 sample intervals, the window is defined to be 30 sample points (e.g. 14 before and 15 points after the R-wave sense point and including the R-wave sense point).

In other embodiments, the number of sample points in the morphology analysis window may be defined as a fixed number of sample points greater than the R-wave width, for example the R-wave width plus 12 sample points. In another example, the number of sample points defining the morphology analysis window may be computed as the R-wave width plus a rounded or truncated percentage of the R-wave width. For example, the morphology analysis window may be defined as the R-wave width plus fifty percent of the R-wave width (i.e. 150% of the R-wave width), up to a maximum of the total alignment window or some portion less than the total alignment window.

The morphology window is applied to both the unknown beat and the template. With the template and unknown cardiac signal aligned within the alignment window, the same number of sample points taken prior to and after the unknown beat alignment point is taken prior to and after the template alignment point.

After setting the morphology analysis window, a morphology metric of the similarity between the unknown signal and the template is computed at block 306. In one embodiment, the NWAD is computed. Different methods maybe used to compute a NWAD. In an illustrative method, the NWAD is computed by normalizing the absolute amplitude of each of the unknown beat sample points and the template sample points within the morphology window by a respective absolute maximum peak amplitude value. A waveform area difference is then calculated by summing the absolute amplitude differences between each aligned pair of normalized sample points in the unknown signal and in the template over the morphology window.

This waveform area difference may be normalized by a template area. The template area is computed as the sum of all of the absolute values of the normalized template sample points in the morphology window. The NWAD is then calculated as the ratio of the waveform area difference to the template area. The NWAD for the aligned signals is stored.

This NWAD may be compared to a threshold to classify the unknown beat as matching the template based on a high correlation between the unknown beat and the template evidenced by a NWAD exceeding a match threshold. One or more NWADs may be computed for a given unknown beat. In the example shown by flow chart 300, additional NWADs are computed by shifting the aligned template relative to the already aligned unknown signal by one or more sample points at block 308. In one embodiment, the template is shifted by one sample point to the right, two sample points to the right, one sample point to the left and two sample points to the left to obtain five different alignments of the template and unknown signal. For each template alignment, i.e. with alignment points aligned exactly and with template and unknown signal alignment points shifted relative to each other by one point and two points in each direction, a NWAD is computed at block 310. In this way, five NWADs are computed to measure the similarity between the unknown beat and the template (in aligned and shifted positions).

At block 312, the NWAD having the greatest value is selected as the morphology metric for the unknown beat and is compared to a match threshold. If the maximum NWAD meets or exceeds the match threshold, the beat is classified as originating in the same chamber as the known template. For example, if a NSR template is established, the beat is classified as a supraventricular beat when the NWAD meets the morphology match threshold. Otherwise, the unknown beat is classified as a VT/VF beat.

This beat classification continues for a required number of beats to determine if VT/VF detection criteria are satisfied. For example, once rate-based detection criteria are met, a required number of consecutive or non-consecutive VT/VF beats classified according to the methods described herein may confirm a VT/VF detection. If satisfied, the processing and control module controls the signal generator to deliver a defibrillation shock therapy to treat the detected VT/VF.

Figure 8:
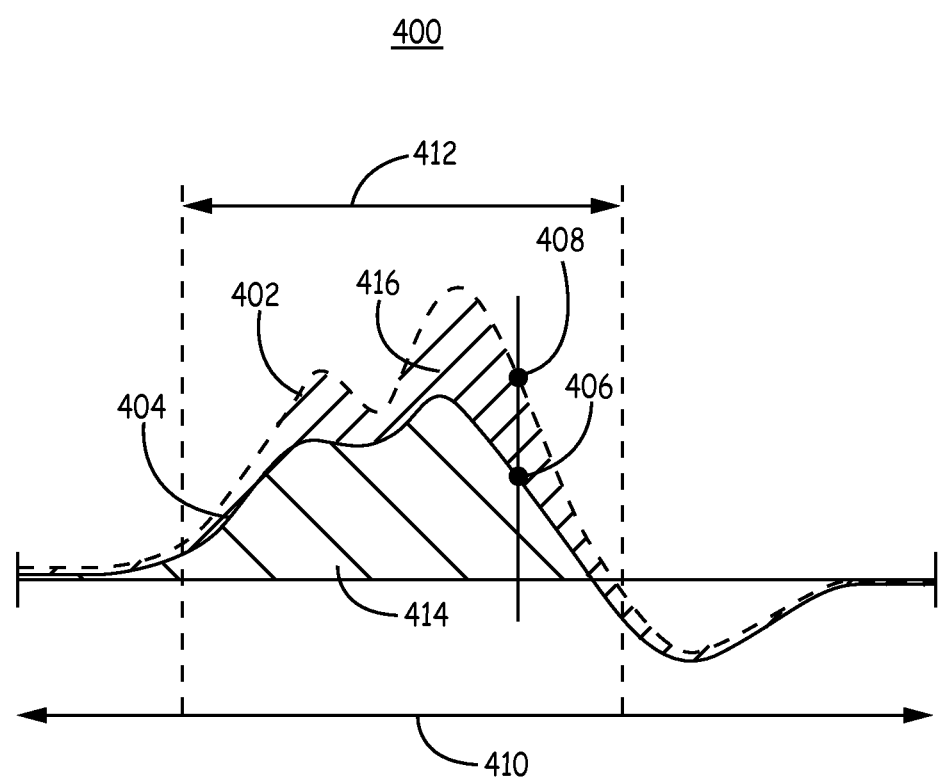
FIG. 8 is a plot of an aligned unknown signal and template illustrating a technique for computing a normalized waveform area difference (NWAD) according to one embodiment.

FIG. 8 is a plot 400 of an aligned unknown signal 402 and template 404 illustrating a technique for computing a NWAD according to one embodiment. In this example, the unknown raw ECG signal 402 and the raw ECG signal template 404 (ensemble average of n raw signals aligned using fourth order difference signal) are used for determining a morphology match metric over a morphology analysis window 412. The width of the morphology analysis window 412 and the alignment of the unknown signal 402 and template 404 are based on analysis of fourth order difference.

The raw ECG signal 402 provided to the processor and control module 110 by the sensing module 102 is aligned with template 404 of the raw ECG signal established during NSR. The template alignment point 406 is identified from the ensemble averaged fourth order difference signal as the maximum absolute pulse amplitude value. The unknown signal alignment point 408 is identified from the fourth order difference signal of the unknown raw ECG signal 402. The unknown signal alignment point 408 is the maximum absolute pulse amplitude value having the same polarity as the template alignment point 406.

After aligning the template 404 with the unknown raw ECG signal 402 over an alignment window 410, a morphology window 412 is set. The morphology window 412 is a subset of, i.e. shorter than or fewer sample points than, the alignment window 410. The morphology window 412 is set based on an R-wave width measured from the fourth order difference signal of the unknown signal as described below in conjunction with FIG. 9. The morphology analysis window 412 is set in response to the R-wave width measurement as some sample number greater than the R-wave width, as described above.

The template area 414 is computed as the sum of all of the normalized absolute values of the template sample points within the morphology analysis window 412. The values are normalized by the absolute value of the maximum amplitude of the template. The waveform area difference 416 is computed as the summation of the absolute values of the differences between the aligned normalized absolute values of the unknown ECG signal sample points and the normalized absolute values of the template sample points. The NWAD is the ratio of the waveform area difference 416 to the template area 414.

FIG. 9 is a plot 500 of an unknown fourth order difference signal 502 aligned with a fourth order difference template 504 illustrating a technique for determining an R-wave width and computing a NWAD according to another embodiment. In this example, the fourth order difference signal 502 of the unknown raw ECG signal is aligned with a fourth order difference signal template 504 for determining a morphology match metric over a morphology analysis window 512.

The unknown fourth order difference signal 502 is derived from the unknown raw ECG signal provided to the processor and control module 110 by the sensing module 102 and is aligned with the fourth order difference template 504 established during NSR. The template alignment point 506 is identified as the maximum absolute pulse amplitude value of the fourth order difference template. The unknown signal alignment point 508 is identified as the maximum absolute pulse amplitude value having the same polarity as the template alignment point 506. The unknown fourth order difference signal 502 is shifted over the alignment window 510 by an alignment shift required to align the unknown signal alignment point 508 with the template alignment point 506 as shown.

After aligning the template 504 with the unknown fourth order difference signal 502 over alignment window 510, a morphology window 512 is set. The morphology window 512 is a subset of the alignment window 510 and is based on an R-wave width 540 measured from the unknown fourth order difference signal 502.

The R-wave width 540 is measured by determining the difference between an R-wave onset point 524 and an R-wave offset point 534 of the fourth order difference signal 502 of the unknown beat. In order to determine an R-wave onset point 524, a maximum positive pulse peak amplitude 520 is measured. An onset threshold 522 is set as a proportion of the maximum positive pulse peak amplitude 520. In one embodiment, the onset threshold 522 is set as one-eighth of the maximum positive pulse peak amplitude 520. The onset point 524 is identified as the first point to the left of the maximum positive pulse peak crossing the onset threshold 522, i.e. equal to or greater than the onset threshold 522.

The offset point 534 is identified by setting an offset threshold 532. The offset threshold is a proportion of a maximum negative pulse peak amplitude 530. The offset point 534 is identified as the first point crossing the offset threshold 532 to the right of the maximum negative pulse. The difference between the onset point 524 and the offset point 534 is measured as the R-wave width 540. The morphology analysis window 512 is set in response to the R-wave width measurement as some sample number greater than the R-wave width 540, as described previously.

In other examples, the maximum negative pulse may occur earlier in the alignment window than the maximum positive pulse. If this is the case, the onset threshold is set as a proportion of the maximum negative pulse peak amplitude and the onset point is determined as the first point crossing the onset threshold to the left of the maximum negative peak. Likewise, the offset threshold is set as a proportion of the maximum positive pulse peak amplitude, and the offset point is determined as the first point to the right of the maximum positive pulse to cross the offset threshold.

The morphology analysis window 512 may be centered on an R-wave sense signal. In some embodiments, the morphology analysis window 512, determined from the fourth order difference signal 502, is applied to the unknown raw ECG signal aligned with a raw ECG signal template, for example window 412 as shown in FIG. 8. The morphology match metric is determined from the raw ECG signal 402 and template 404. In the example shown in FIG. 9, the morphology analysis window 512 is applied to the fourth order difference signal 502; the morphology match metric is determined from the fourth order difference signal 502 and fourth order difference template 504.

The template area 514 is computed as the sum of all of the normalized absolute values of the template sample points within the morphology window 512. The values are normalized by the absolute value of the maximum amplitude of the template 504 (in this example point 508). The waveform area difference 516 is computed as the summation of the absolute differences between the aligned normalized absolute values of the unknown fourth order difference signal sample points and the normalized absolute values of the template sample points. The NWAD is the ratio of the waveform area difference 516 and the template area 514. This NWAD is compared to a match threshold to classify the unknown beat corresponding to the fourth order difference signal 502 as a supraventricular beat or a beat originating in the ventricles. Detection of beats arising from the ventricles can be used in detecting shockable tachyarrhythmias, i.e. VT or VF originating in the ventricles.

Thus, a method and apparatus for performing morphology analysis for detection and discrimination of tachyarrhythmias have been presented in the foregoing description with reference to specific embodiments. It is appreciated that various modifications to the referenced embodiments may be made without departing from the scope of the disclosure as set forth in the following claims.

The invention claimed is:

1. A method for classifying cardiac beats for use in detecting cardiac rhythms, comprising:
sensing a cardiac signal over a plurality of cardiac cycles using a plurality of electrodes coupled to a sensing module;
determining a template of a known cardiac signal in response to the cardiac signal sensed over the plurality of cardiac cycles;
determining a template alignment point from the template of the known cardiac signal;
sensing a cardiac signal having an unknown morphology over a plurality of cardiac cycles;
determining a fourth order difference signal by applying a fourth order difference function to the cardiac signal having an unknown morphology;
determining an alignment point for the cardiac signal having an unknown morphology from the fourth order difference signal;
aligning the template and the cardiac signal having an unknown morphology across an alignment window by aligning the template alignment point and the alignment point of the cardiac signal having an unknown morphology;
determining a first morphology match metric between the aligned template and the cardiac signal having an unknown morphology; and
classifying the cardiac signal having an unknown morphology based on the first morphology match metric.

2. The method of claim 1, wherein determining the template comprises:
determining a fourth order difference signal of the cardiac signal over each of the plurality of cardiac cycles;
determining alignment points from the fourth order difference signal for each of the plurality of cardiac cycles;
aligning the plurality of cardiac cycle signals by aligning the alignment points for each of the plurality of cardiac cycles; and
averaging the aligned plurality of cardiac cycle signals.

3. The method of claim 1, wherein determining the template comprises:
determining a fourth order difference signal for the cardiac signal over each of the plurality of cardiac cycles;
determining a alignment points from the fourth order difference signal for each of the plurality of cardiac cycles;
aligning the plurality of fourth order difference signals of each of the cardiac cycle signals by aligning the alignment points; and
averaging the aligned plurality of fourth order difference signals.

4. The method of claim 1, wherein determining the template alignment point comprises determining a peak amplitude and a polarity of a dominant pulse of a fourth order difference signal obtained from the template.

5. The method of claim 4, wherein determining the alignment point for the cardiac signal having an unknown morphology comprises:
determining a peak amplitude of a dominant pulse of the fourth order difference signal of the cardiac signal having an unknown morphology that matches the polarity of the template alignment point.

6. The method of claim 1, further comprising:
after aligning the template alignment point and the alignment point of the cardiac signal having an unknown morphology, shifting the template by shifting the template alignment point relative to the alignment point of the cardiac signal having an unknown morphology by at least one sample point;
determining a second morphology match metric as a measure of a similarity between the shifted template and the cardiac signal having an unknown morphology;
selecting a greatest one of the first morphology match metric and the second morphology match metric; and
classifying the cardiac signal having an unknown morphology in response to the selected one of the first and second morphology match metrics.

7. The method of claim 1, further comprising:
after aligning the template alignment point and the alignment point of the cardiac signal having an unknown morphology, shifting the template a plurality of times by shifting the template alignment point relative to the alignment point of the cardiac signal having an unknown morphology by at least one sample point to obtain a plurality of alignments between the template and the cardiac signal having an unknown morphology;
determining a morphology match score for each one of the plurality of alignments;
determining a greatest one of the first morphology match metric and the morphology match metrics for the plurality of alignments; and
classifying the cardiac signal having an unknown morphology in response to the determined greater one of the first morphology match metric and the morphology match metrics for the plurality of alignments.

8. The method of claim 1, wherein determining the first morphology match metric comprises determining a normalized waveform area difference between the aligned template and the cardiac signal having an unknown morphology.

9. The method of claim 1, wherein determining the first morphology match metric comprises determining a fourth order difference signal of the template; and determining the morphology match metric between the fourth order difference signal of the template and the fourth order difference signal of the cardiac signal having an unknown morphology.

10. A medical device for classifying cardiac beats for use in detecting cardiac rhythms, comprising:

a plurality of electrodes for sensing an electrocardiogram (ECG) signal;

a sensing module coupled to the electrodes for sensing a cardiac signal over a plurality of cardiac cycles and a cardiac signal having an unknown morphology over a plurality of cardiac cycles; and a processor coupled to the sensing module and configured to:

determine a template of a known cardiac signal in response to the cardiac signal sensed over the plurality of cardiac cycles;

determine a template alignment point from the template of the known cardiac signal;

determine a fourth order difference signal by applying a fourth order difference function to the cardiac signal having an unknown morphology;

determine an alignment point for the cardiac signal having an unknown morphology from the fourth order difference signal;

align the template and the cardiac signal having an unknown morphology across an alignment window by aligning the template alignment point and the alignment point of the signal having an unknown morphology; and determine a first morphology match metric measuring a similarity between the aligned template and the cardiac signal having an unknown morphology; and classify the cardiac signal having an unknown morphology based on the first morphology match metric.

11. The device of claim 9, wherein determining the template comprises:

determining a fourth order difference signal of the cardiac signal over each of the plurality of cardiac cycles;

determining alignment points from the fourth order difference signal for each of the plurality of cardiac cycles;

aligning the plurality of cardiac cycle signals by aligning the alignment points for each of the plurality of cardiac cycles; and averaging the aligned plurality of cardiac cycle signals.

12. The device of claim 9, wherein determining the template comprises:

determining a fourth order difference signal for the cardiac signal over each of the plurality of cardiac cycles;

determining alignment points from the fourth order difference signal for each of the plurality of cardiac cycles;

aligning the plurality of fourth order difference signals of each of the cardiac cycle signals by aligning the alignment points; and averaging the aligned plurality of fourth order difference signals.

13. The device of claim 9, wherein determining the template alignment point comprises determining a peak amplitude and a polarity of a dominant pulse of a fourth order difference signal obtained from the template.

14. The device of claim 12, wherein determining the alignment point for the cardiac signal having an unknown morphology comprises:

determining a peak amplitude of a dominant pulse of the fourth order difference signal of the cardiac signal having an unknown morphology that matches the polarity of the template alignment point.

15. The device of claim 9, wherein the processor is further configured to:

determine an R-wave onset and an R-wave offset for each of a plurality of cardiac cycles of the fourth order difference signal of the cardiac signal having an unknown morphology;

determine an R-wave width in response to a difference between the R-wave onset and the R-wave offset;

determine a morphology analysis window in response to the R-wave width; and determine the first morphology match metric across the morphology analysis window.

16. The device of claim 14, wherein the morphology analysis window comprises a first number of sample points of the cardiac signal having an unknown morphology, and the alignment window comprises a second number of sample points of the cardiac signal having an unknown morphology, wherein the second number is greater than the first number.

17. The device of claim 9, further comprising:

after aligning the template alignment point and the alignment point of the cardiac signal having an unknown morphology, shifting the template by shifting the template alignment point relative to the alignment point of the cardiac signal having an unknown morphology by at least one sample point;

determining a second morphology match metric as a measure of a similarity between the shifted template and the cardiac signal having an unknown morphology;

selecting a greatest one of the first morphology match metric and the second morphology match metric; and classifying the cardiac signal having an unknown morphology in response to the selected one of the first and second morphology match metrics.

18. The device of claim 9, wherein the processor is further configured to:

after aligning the template alignment point and the alignment point of the cardiac signal having an unknown morphology, shift the template a plurality of times by shifting the template alignment point relative to the alignment point of the cardiac signal having an unknown morphology by at least one sample point to obtain a plurality of alignments between the template and the cardiac signal having an unknown morphology;

determine a morphology match score for each one of the plurality of alignments;

determine a greatest one of the first morphology match metric and the morphology match metrics for the plurality of alignments; and classify the cardiac signal having an unknown morphology in response to the determined greatest one of the first morphology match metric and the morphology match metrics for the plurality of alignments.

19. The device of claim 9, wherein determining the first morphology match metric comprises determining a normalized waveform area difference between the aligned template and the cardiac signal having an unknown morphology.

20. The device of claim 9, wherein determining the first morphology match metric comprises determining a fourth order difference signal of the template; and determining the morphology match metric between the fourth order difference signal of the template and the fourth order difference signal of the cardiac signal having an unknown morphology.

21. A non-transitory, computer-readable medium storing a set of instructions, which when executed by a processor of a medical device causes the device to:

sense a cardiac signal over a plurality of cardiac cycles using a plurality of electrodes coupled to a sensing module;

generate a template of a known cardiac signal in response to the cardiac signal sensed over the plurality of cardiac cycles;

determine a template alignment point from the template of the known cardiac signal;

sense a cardiac signal having an unknown morphology over a plurality of cardiac cycles;

determine a fourth order difference signal by applying a fourth order difference function to the cardiac signal having an unknown morphology;

determine an alignment point for the cardiac signal having an unknown morphology from the fourth order difference signal;

align the template and the cardiac signal having an unknown morphology across an alignment window by aligning the template alignment point and the alignment point of the signal having an unknown morphology; and determine a morphology match metric measuring a similarity between the aligned template and the cardiac signal having an unknown morphology; and classify the cardiac signal having an unknown morphology based on the first morphology match metric.

* * * * *